US00PP23694P2

(12) United States Plant Patent
Bradford

(10) Patent No.: US PP23,694 P2
(45) Date of Patent: Jul. 2, 2013

(54) INTERSPECIFIC TREE NAMED 'BLACKRED IX'

(50) Latin Name: ***Prunus* sp.**
Varietal Denomination: Blackred IX

(76) Inventor: Lowell Glen Bradford, Le Grand, CA (US)

( * ) Notice: Subject to any disclaimer, the term of this patent is extended or adjusted under 35 U.S.C. 154(b) by 56 days.

(21) Appl. No.: 13/374,019

(22) Filed: Dec. 8, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP20,863 P2 3/2010 Bradford

*Primary Examiner* — Annette Para

(57) ABSTRACT

The present invention relates to an interspecific tree and more particularly to a medium size, vigorous, hardy, and productive tree. Being self-unfruitful, the present variety requires cross pollination from an apricot, interspecific, or plum that blooms during the late season. The present variety produces a very heavy bloom, but is pollen deficient and should have pollinators grafted in the center of the tree to entice good bee activity for sufficient pollination. The fruit matures under the ecological conditions described during the latter part of August, with first picking on Aug. 29, 2011. The fruit is uniformly large in size, dark purplish red in skin color, clingstone in type, globose in shape, full red in flesh color, firm in texture, and very good in flavor.

1 Drawing Sheet

Botanical classification: *Prunus* sp.
Varietal denomination: 'BLACKRED IX'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred IX'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 1997 one such house containing an unpatented red plum, code named '19P442', was crossed by me in this manner. To pollinate this red plum, I selected bouquets from several sources of apricot and interspecific hybrid trees without keeping specific written details. Upon reaching maturity the fruit from this red plum tree was harvested and the seeds were removed, cracked, stratified and germinated as a group with the label "H5". They were grown as seedlings on their own root in my greenhouse and upon reaching dormancy transplanted to a cultivated area of my experimental orchard located near Le Grand, Calif. in Merced County (San Joaquin Valley). During the summer of 2002 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, '19P442' plum (unpatented), by producing fruit that is red in flesh color and dark red to black in skin color, but is quite distinguished therefrom by producing fruit that is sweeter in flavor, that is much larger in size, and that matures about two months later.

The present variety is most similar to 'Blackred VIII' (U.S. Plant Pat. No. 20,863) interspecific tree by being self-unfruitful and by producing fruit that is clingstone in type, that is mostly dark red to black in skin color, that is large in size, that is sweet in flavor, and that matures in the latter part of August, but is distinguished therefrom by blooming much later, by being pollen deficient, and by producing fruit that is globose instead of oblate in shape, that is full red instead of pink in flesh color, and that matures about five days later.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the late season. The present variety produces a very heavy bloom, but is pollen deficient and should have pollinators grafted in the center of the tree to entice good bee activity for sufficient pollination. The fruit matures under the ecological conditions described during the latter part of August, with first picking on Aug. 29, 2011. The fruit is uniformly large in size, dark purplish red in skin color, clingstone in type, globose in shape, full red in flesh color, firm in texture, and very good in flavor.

DRAWING

The accompanying photograph consists of five whole fruits positioned to display the characteristics of the skin color and form, four of them shined and one of them with the bloom remaining, one half fruit divided transversely to the suture plane to reveal the flesh and stone, typical leaves, a young tip shoot growth, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Sep. 8, 2011, on a multipled tree utilizing 'Nemagard' rootstock (unpatented) during its tenth growing season. The flower and bud descriptions were developed during the previous blooming season. All major color code designations are by reference to the Inter-Society Color Council, National Bureau of Standards. Common color names are also used occasionally.

PARENTAGE

Seed parent: '19P442' plum (unpatented).
Pollen parent: Unknown.

TREE

Size: Medium, reaching a height of 13' [3.96 m.] and a spread of 7' [2.13 m.] after ten growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and open.

Form: Pruned to a central leader form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'Plumsweet IV' (U.S. Plant Pat. No. 16,461) interspecific tree.

Bearing: Fairly certain bearer, weather dependent, crop failures are rare.

Trunk:

*Size*.—Medium, reaching a maximum diameter of 3¾" [95.3 mm.] after the tenth growing season.

*Texture*.—Shaggy.

*Bark color*.—A Dark grayish yellowish brown [81. d.gy.yBr] and Dark yellowish brown [78. d.yBr] variegation with Light yellowish brown [76. l.yBr] crevices present.

*Lenticels*.—Approximate Number Per Square Inch: 7. Color: Deep orange [51. deep O]. Average Size: 3/8" [9.5 mm.]. Shape: Elongated, eye-shaped.

Branches:

*Size*.—Diameter of the lowest horizontal limb is 2¾" [69.9 mm.]. Diameter of first hanger is 1" [25.4 mm.].

*Texture*.—Smooth on first year wood, increasing roughness with age.

*Color*.—1st Year Wood Topside: Grayish red [19. gy.R]. 1st Year Wood Underside: Brilliant yellow green [116. brill.YG]. 2nd Year Wood: A Deep brown [56. deep Br] and Grayish yellowish brown [80. gy.yBr] variegation. Older Wood: A Dark grayish yellowish brown [81. d.gy.yBr] and Dark yellowish brown [78. d.yBr] variegation.

*Lenticels*.—Number Per Square Inch: About 100 on second year wood. Color: Light yellowish brown [76. l.yBr]. Average Size: 1/32" [0.8 mm.]. Shape: Elongated, eye-shaped.

Leaves:

*Size*.—Medium to large. Average Length: 4½" [114.3 mm.]. Average Width: 2 1/16" [52.4 mm.].

*Arrangement*.—Alternate.

*Thickness*.—Medium.

*Form*.—Elliptical.

*Apex*.—Acuminate.

*Base*.—Acute with an average angle base angle of 70 degrees.

*Surface*.—Smooth.

*Color*.—Dorsal Surface: Dark yellowish green [137. d.yG]. Ventral Surface: Moderate yellowish green [136. m.yG].

*Margin*.—Finely serrate.

*Venation*.—Pinnately net veined.

*Petiole*.—Average Length: ½" [12.7 mm.]. Average Thickness: 1/16" [1.6 mm.]. Color: Light yellow green [119. l.YG] with Moderate red [15. m.R] areas where exposed to direct sunlight.

*Stipules*.—Number: 2 per leaf at the young stage, up to 6 per growing tip. Average Length: 5/16" [7.9 mm.]. Color: Brilliant yellow green [116. brill.YG] becoming Grayish brown [61. gy.Br] with age.

*Glands*.—Number: Mostly 2 per leaf. Position: Alternately positioned on the petiole and base of the leaf blade. Size: Medium. Form: Globose. Color: Brilliant yellow green [116. brill.YG] becoming Dark yellowish brown [78. d.yBr] with age. Leaf buds: Pointed, medium.

Flower buds:

*Hardiness*.—Hardy, with respect to central California winters.

*Diameter*.—Typically 3/16" [4.8 mm.] 1 week before bloom.

*Length*.—Typically ⅜" [9.5 mm.] 1 week before bloom.

*Form*.—Not appressed.

*Surface*.—Pubescent.

*Tip color*.—White [263. White] with a very slight Light Pink [4. l.Pk] tinge on some.

Flowers: Perfect, complete, perigynous, usually a single pistil, typically thirty or more stamens, five sepals and petal locations alternately positioned.

*Average flower diameter*.—1" [25.4 mm.].

*Number of petals*.—Five, no double blossoms observed.

*Petal shape*.—Oval to circular.

*Petal margin*.—Entire, smooth to slightly wavy.

*Average petal diameter*.—9/16" [14.3 mm.].

*Average petal length*.—9/16" [14.3 mm.].

*Petal apex*.—Rounded.

*Petal base*.—Obtuse.

*Petal color*.—White [263. White] on both sides.

*Anther color*.—Pale yellow [89. p.Y].

*Stigma color*.—Light greenish yellow [101. l.gY].
*Sepal color*.—Strong yellow green [117. s.YG] on the outer surface with slight Grayish red [19. gy.R] tinge toward the edges on some.
*Sepal length*.—3/16" [4.8 mm.].
*Sepal width*.—5/32" [4.0 mm.].
*Sepal apex*.—Rounded to elliptical to match the width and length.
*Sepal margin*.—Fairly smooth, with slight serration toward the apex.
*Average pistil length*.—9/16" [14.3 mm.].
*Average stamen length*.—7/16" [11.1 mm.].
*Fragrance*.—Moderate.
*Pollen production*.—Deficient.
*Blooming period*.—Mid to late, two days after 'Santa Rosa' plum (unpatented).
*Bloom density*.—Very heavy.
*Number per cluster*.—2 to 10, average 6.
*Onset of bloom*.—One percent on Mar. 6, 2011.
*Date of full bloom*.—Mar. 13, 2011.
*Duration of bloom*.—One to two weeks, dependent on ambient temperature.

FRUIT

Maturity when described: Firm ripe, Sep. 8, 2011.
Date of first picking: Aug. 29, 2011.
Date of last picking: Sep. 14, 2011.
Size: Uniform, large.
*Average diameter axially*.—2⅝" [66.7 mm.].
*Average diameter across cheek plane*.—2¾" [69.9 mm.].
*Average diameter across suture plane*.—2⅝" [66.7 mm.].
*Typical weight*.—6.6 ounces [187 grams].
Form: Uniform, globose, symmetrical.
*Longitudinal section form*.—Oval.
*Transverse section through diameter*.—Round.
Suture: An inconspicuous line located in a shallow trough extending from the base to the pistil point.
Ventral surface: Rounded.
Lips: Virtually no lips.
Cavity: Flaring, circular, suture showing on one side, stem markings rarely occurring.
*Depth*.—7/16" [11.1 mm.].
*Breadth*.—1⅛" [28.6 mm.].
Base: Truncate, slightly cordate if viewed parallel to the suture.
Apex: Rounded.
Pistil point: An inconspicuous Light reddish brown [42. l.rBr] dot.
Stem: Large.
*Average length*.—5/16" [7.9 mm.].
*Average width*.—3/32" [2.4 mm.].
Skin:
*Thickness*.—Medium.
*Surface*.—Smooth.
*Tenacity*.—Tenacious to the flesh.
*Astringency*.—Slight.
*Tendency to crack*.—Slight.
*Color*.—Very dark purplish red [260. v.d.pR] over a Very deep red [14. v.deep R] background with Light reddish brown [42. l.rBr] freckling throughout.
*Bloom*.—Abundant.
Flesh:
*Color*.—Very dark red [17. v.d.R] near the skin and Moderate red [15. m.R] toward the stone.
*Surface of pit cavity*.—Covered with Moderate red [15. m.R] broken fibers when twisted away from stone.
*Amygdalin*.—Moderate.
*Juice*.—Abundant, rich.
*Texture*.—Firm, crisp, melting.
*Fibers*.—Abundant, fine.
*Ripens*.—Fairly even, somewhat earliest at apex.
*Flavor*.—A very sweet blend of mild acid and sugar, typically 18 to 20 brix.
*Aroma*.—Very slight.
*Eating quality*.—Very good.

STONE

Type: Clingstone.
Form: Oval.
Hilum: Narrow.
Base: Straight.
Apex: Acute, with a small 1/16" [1.6 mm.] protruding tip.
Sides: Equal.
Surface: Rough throughout.
External color of stone: Deep yellowish brown [75. deep yBr] when first removed.
Pit wall color when cracked: Light yellowish brown [76. l.yBr].
Cavity surface color: Strong yellowish brown [74. s.yBr].
Average pit wall thickness: 1/16" [1.6 mm.].
Average width: ⅝" [15.9 mm.].
Average length: ⅞" [22.2 mm.].
Average breadth: ⅜" [9.5 mm.].
Tendency to split: None observed.
Kernel:
*Form*.—Oval.
*Skin color*.—Light yellowish brown [76. l.yBr] when dry.
*Pellicle color*.—Deep yellowish brown [75. deep yBr].
*Vein color*.—Deep yellowish brown [75. deep yBr].
*Taste*.—Bitter.
*Viable*.—Yes.
*Average width*.—⅜" [9.5 mm.].
*Average length*.—⅝" [15.9 mm.].
*Amygdalin*.—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Blackred VIII' (U.S. Plant Pat. No. 20,863) interspecific tree by being self-unfruitful and by producing fruit that is clingstone in type, that is mostly dark red to black in skin color, that is large in size, that is sweet in flavor, and that matures in the latter part of August, but is distinguished therefrom by blooming much later, by being pollen deficient, and by producing fruit that is globose instead of oblate in shape, that is full red instead of pink in flesh color, and that matures about five days later.

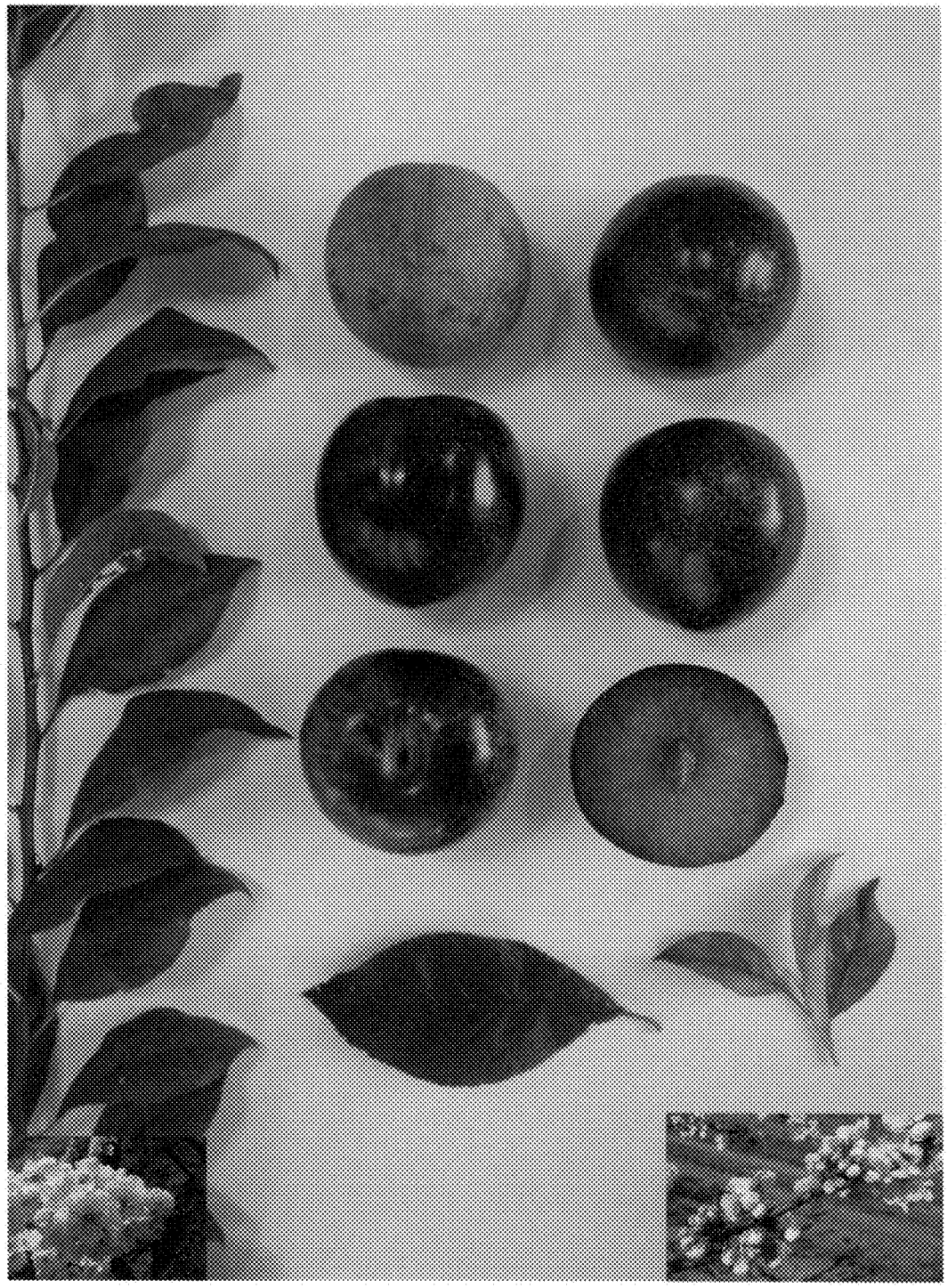

* * * * *